(12) United States Patent
Melchert et al.

(10) Patent No.: US 9,772,259 B2
(45) Date of Patent: Sep. 26, 2017

(54) METHOD FOR CALIBRATING AN X-RAY TESTING SYSTEM FOR A TIRE TYPE AND METHOD FOR CHECKING THE POSITION OF CORDS IN A TIRE

(71) Applicant: YXLON INTERNATIONAL GMBH, Hamburg (DE)

(72) Inventors: Juergen Melchert, Bad Oldesloe (DE); Klaus Bavendiek, Norderstedt (DE)

(73) Assignee: YXLON INTERNATIONAL GMBH, Hamburg (DE)

( * ) Notice: Subject to any disclaimer, the term of this patent is extended or adjusted under 35 U.S.C. 154(b) by 239 days.

(21) Appl. No.: 14/763,248

(22) PCT Filed: Jan. 28, 2014

(86) PCT No.: PCT/EP2014/000213
§ 371 (c)(1),
(2) Date: Nov. 2, 2015

(87) PCT Pub. No.: WO2014/114467
PCT Pub. Date: Jul. 31, 2014

(65) Prior Publication Data
US 2016/0103040 A1    Apr. 14, 2016

(30) Foreign Application Priority Data
Jan. 28, 2013   (DE) .................. 10 2013 001 456

(51) Int. Cl.
*G01N 23/04*     (2006.01)
*G01M 17/03*     (2006.01)
*G01N 23/18*     (2006.01)

(52) U.S. Cl.
CPC .......... *G01M 17/028* (2013.01); *G01N 23/04* (2013.01); *G01N 23/185* (2013.01); *G01N 2223/303* (2013.01); *G01N 2223/627* (2013.01)

(58) Field of Classification Search
CPC ........ G01N 23/00; G01N 23/02; G01N 23/04; G01N 23/08; G01N 23/083; G01N 23/18;
(Continued)

(56) References Cited

U.S. PATENT DOCUMENTS

| 2,272,893 A | 2/1942 | Bosomworth |
| 3,803,415 A | 4/1974 | Fox |

(Continued)

FOREIGN PATENT DOCUMENTS

| EP | 0315099 A2 | 5/1989 |
| EP | 1867971 B1 | 12/2007 |
| GB | 1381302 A | 1/1975 |

*Primary Examiner* — Jurie Yun
(74) *Attorney, Agent, or Firm* — Leydig, Voit & Mayer, Ltd.

(57) ABSTRACT

A method for calibrating an X-ray inspection system for a tire. The X-ray inspection system includes an X-ray tube, a linear X-ray detector, and a manipulator for the tire. The method includes moving one of the X-ray tube, the linear X-ray detector, and the manipulator along a travel path from a set starting position to a set end position, capturing, at a preset reading rate during the movement of one of the X-ray tube, the linear X-ray detector, and the manipulator, a continuous capture of X-ray radiography images of a cord within the tire, tracking the cord using successive X-ray radiography images, and deducing an absolute position of the cord using a total shift of the cord in the X-ray radiography images between the starting position and the end position and using known geometric data.

8 Claims, 7 Drawing Sheets

(58) Field of Classification Search
CPC ........... G01N 23/185; G01N 2223/303; G01N 2223/627; G01M 17/03; G01M 17/028
USPC ............................................ 378/58, 61, 207
See application file for complete search history.

(56) References Cited

U.S. PATENT DOCUMENTS

| | | | |
|---|---|---|---|
| 3,952,195 A | | 4/1976 | Heisner |
| 4,857,749 A | * | 8/1989 | McCarty ................ G01B 11/14 250/559.16 |
| 5,083,306 A | | 1/1992 | Steffel |
| 5,737,383 A | * | 4/1998 | Noda .................. G01M 17/028 378/57 |

* cited by examiner

METHOD FOR CALIBRATING AN X-RAY TESTING SYSTEM FOR A TIRE TYPE AND METHOD FOR CHECKING THE POSITION OF CORDS IN A TIRE

CROSS REFERENCE TO RELATED APPLICATIONS

This application is a U.S. National Phase application under 35 U.S.C. §371 of International Application No. PCT/EP2014/000213 (WO 2014/114467), filed on Jan. 28, 2014, and claims benefit to German Patent Application No. DE 10 2013 001 456.5, filed Jan. 28, 2013.

FIELD

The invention relates to a method for calibrating an X-ray inspection system for a tire, and to a method for inspecting the position of cords in a tire of a particular tire type using an X-ray inspection system after carrying out a calibration.

BACKGROUND

HGV and car tires today have a fixed cord geometry which is embedded in rubber. The cords are either formed as metal wires or from plastic fibres. In order to be able to comment on the quality of an individual tire, it must be determined for this tire on an individual basis whether the predetermined geometry of the cords is also realized or if there are deviations from this. Both the relative position of the individual cords in relation to each other and the absolute position of the cords in the rubber, thus for example their distance from the tread of the tire, are relevant for assessing the quality. For technological reasons, in different tires the individual components of the tires are represented on different scales in the X-ray image. The inspection specifications applicable in the X-ray inspection of tires sometimes include measurement indications. In order to be able to determine the deviation from these measurement indications, it is necessary to calibrate the X-ray inspection system, used for the inspection, uniquely for the relevant tires. An X-ray radiography procedure using a line detector which is formed U-shaped and which thus surrounds the tire over its two side walls and the tread is routinely implemented today for the inspection of the cords.

If a specific tire type is inspected, it is necessary to calibrate the inspection system, which routinely comprises an X-ray tube and an X-ray detector, between which a movable manipulator is arranged, on which the tire to be inspected is clamped. A two-dimensional X-ray image only results when the tire turns, while the line detector is read in a clocked manner.

In order to be able to carry out a meaningful assessment of the quality of the tires to be inspected, of the new tire type, in the calibration the internal and external geometry of this tire type must either be estimated, which is very imprecise, or be detected in the X-ray radiography beam using strip-shaped test pieces which are placed over the internal and external walls. From the results obtained thereby, in the subsequent inspection of a specific tire, the position of the cords can only be estimated. Moreover, this type of calibration is very time-consuming. In addition, such a calibration must be carried out by an experienced operator, because he has to carry out a visual check.

After the calibration of the X-ray inspection system to a new tire type, the individual tires are inspected, according to EP 1 867 971 B1 for example, as follows. The X-ray tube is arranged in a first position relative to the tire and radiography of the tire is carried out. The beams that pass through two particular points on the tire are detected in a detector with respect to their respective coordinate. After that, the X-ray tube is moved from its first position into a second position in the axial direction. There, X-ray beams passing through the two points already detected previously in the first position are detected again by the X-ray detector with respect to their coordinates. The actual coordinates of the first and the second point within the tire, the imaging of which is carried out by the detector, are obtained via geometric observations, in that the respective lines of intersection of the X-ray beams which pass through them are obtained from the two positions of the X-ray tube and the respectively mapped coordinates on the detector. Following this, the actual distance between these two points within the tire is calculated and the length between the first and the second point on the image is converted into an actual distance between the first and the second point.

SUMMARY

In an embodiment, a method for calibrating an X-ray inspection system for a tire, which includes an X-ray tube, a linear X-ray detector, and a manipulator for the tire, is provided. The manipulator is arranged such that the tire is arranged with its tread between the X-ray tube and the X-ray detector. The method includes moving one of the X-ray tube, the linear X-ray detector, and the manipulator along a travel path from a set starting position to a set end position, capturing, at a preset reading rate during the movement of one of the X-ray tube, the linear X-ray detector, and the manipulator, a continuous capture of X-ray radiography images of a cord within the tire, tracking the cord using successive X-ray radiography images, and deducing an absolute position of the cord using a total shift of the cord in the X-ray radiography images between the starting position and the end position and using known geometric data.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An aspect of the invention is to shorten the time-consuming set-up for a new tire type and to enable the geometry of cord plies in the tire to be determined in asubsequent inspection method.

A continuous capture of X-ray radiography images in the X-ray detector may only take place during a continuous movement of one of the three components (X-ray tube, X-ray detector, or X-ray manipulator), a time-saving determination of the "migration" of the cords takes place in the successive X-ray radiography images, wherein the "migration" of an individual cord between two captures is made traceable. As a result of this, an additional estimation of the geometry, or an application of strip-shaped test pieces to the inner or outer wall of the tire, is not necessary. Through such a calibration method, all of the information is available in order to subsequently carry out a very fast and reliable inspection of the cord plies of a large number of tires of the tire type in question. As the detector is a line detector, a succession of light and dark points in a line results if the tire does not turn. To determine the position of an individual cord—a dark point in the X-ray radiography image—the shift in the radiography direction of one of the three components (X-ray tube, X-ray detector, and X-ray manipulator) with tire can be used to determine the absolute position of the cord. If it is now desired to track a particular point—i.e. a cord—which, because of the shifting in the radiography direction of one of the three named components, shifts along the detector line, this point is to be tracked from image acquisition to image acquisition. If the speed of travel in relation to the reading rate of the line detector is suitably chosen, the migration of the cord can be tracked reliably from detector element to detector element.

In and embodiment, the component which is moved is the manipulator. Because of the geometric relationships—in particular the change of the magnification—such a movement of the manipulator is suited to the "migration" of an individual cord in the imaging on the X-ray detector being as large as possible—in comparison with the two other possibilities of moving the X-ray detector or the X-ray tube—and thus leads to a good trackability of the "migration" of the cords in the X-ray radiography images in chronological sequence.

In an embodiment, a further advantageous development of the invention provides that the movement of the component takes place over a travel path of from 50 to 200 mm, preferably 100 mm. Such a travel path is sufficient to effect a good recognizability of the "migration" of the cords and at the same time short enough to require as little time as possible for the calibration.

In an embodiment, a further advantageous development of the invention provides that the travel path runs perpendicularly to the tread of the tire. This represents a simple travel which can be carried out using some of the hitherto already used inspection devices.

In an embodiment, a further advantageous development provides that the reading rate is 0.1 to 10 ms, preferably 0.5 ms. Such a reading rate has the result that good trackability of the individual cords in the successive X-ray radiography images collected is possible.

In an embodiment, a further advantageous development of the invention provides that the speed of the movement of the component is 1 to 2 m/min, preferably 1.5 m/min. Such a speed can be realized well mechanically and can already be carried out using known inspection devices, with the result that it is possible to resort to these. Moreover, it is ensured that, when combined with a reasonable reading rate, sufficient X-ray radiography images can be collected in order to enable a very good tracking of the "migration" of the cords.

A calibration method according to the invention may be carried out before the inspection of the position of the cords, only a single X-ray radiography image needs to be captured in a particular position of the respective tire in order to be able to deduce the absolute position of the cords within the tire using the values obtained in the calibration method. In the radiographic inspection of tires, the X-ray radiography image results from the rotation of the tire between the X-ray tube and the line detector, which is read in a clocked manner. From the succession of the individual line images, a two-dimensional X-ray image results as a developed view of the tire. The X-ray image presents the tire as strips in the rolling direction. Through the preceding calibration (determination of the magnification scale), it is possible to detect the individual tire details in terms of dimensions. Now, for example, the distances of the cords from each other can be stated in a length measurement unit. This makes it much easier to carry out the inspection and brings with it a reliability of the inspection of the cord plies which goes beyond the inspection methods undertaken until now.

Preferably, the X-ray radiography image for the inspection of the respective tire is captured either in the starting position or the end position of the movable component. It is possible to reach each of these two named positions particularly easily, as the moving component only has to be moved to one of its two end stops. Because of this, it is also possible to determine the position very precisely, and thus an extremely reliable inspection is also possible, as the comparison with the data obtained in the preceding calibration method is to be very precisely determined.

Figure 1:
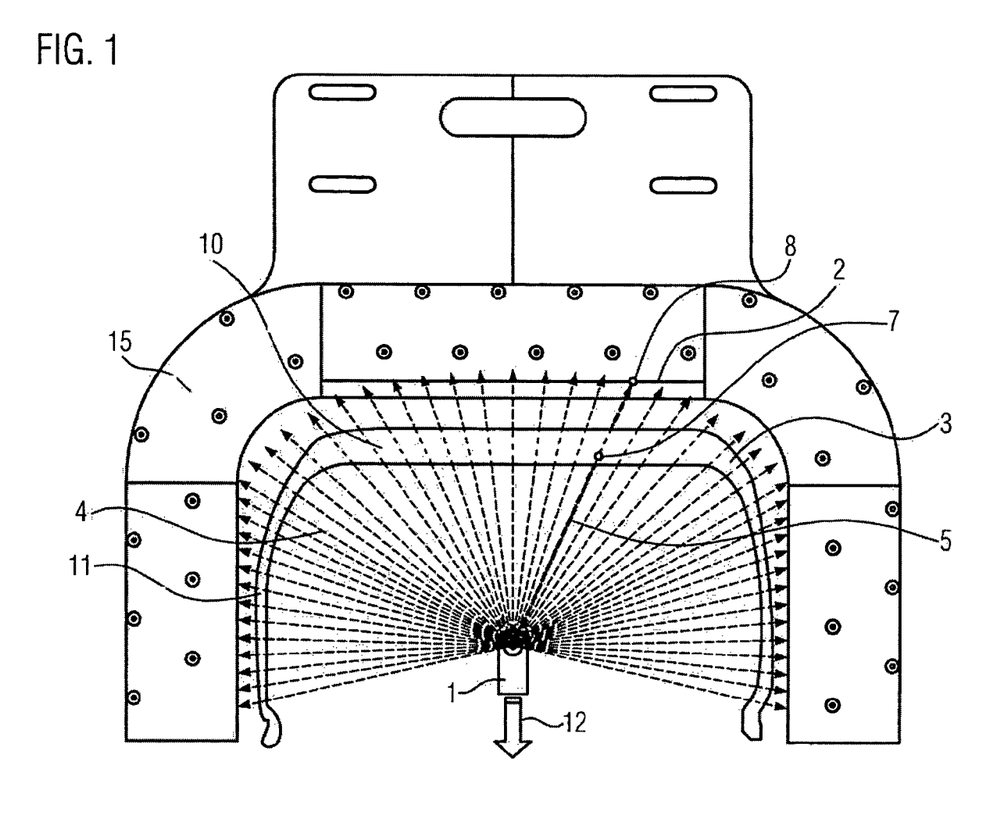
FIG. 1 depicts a schematic partial sectional representation of an X-ray inspection system with tire according to an embodiment of the invention, wherein the X-ray tube is in its starting position.
Figure 2:
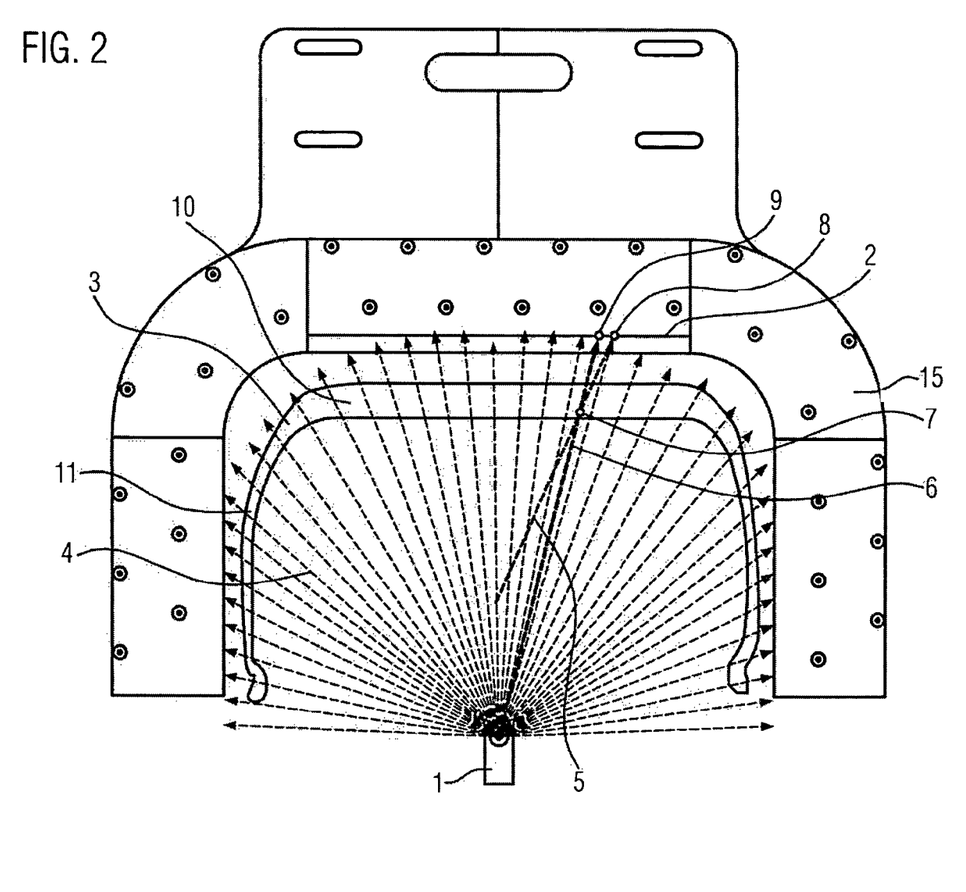
FIG. 2 depicts the X-ray inspection system according to FIG. 1, wherein the X-ray tube is in its end position.

In FIGS. 1 and 2, the extreme positions of an X-ray tube 1 of a first embodiment example of a method according to the invention are represented. As well as the X-ray tube 1, the X-ray inspection system represented for implementing the calibration method has an X-ray detector 2. The X-ray detector 2 represented in the embodiment example is formed as a line detector and is located in a housing 15. For reasons of clarity, the X-ray detector 2 is only represented in the upper part of the housing 15, which runs horizontally in the drawing. In reality, however, the X-ray detector 2 also spans the two U-shaped side arms, which run vertically, and the curved regions arranged between the vertical and horizontal elements. Such a detector type is known from the state of the art, with the result that its more detailed design need not be described further. This also applies to the evaluation units connected to the X-ray detector 2.

Between the X-ray tube 1 and the X-ray detector 2, a tire 3 is arranged, which is fixed on a manipulator (not shown). By means of this manipulator it is at least possible to rotate a tire 3 attached to it about its central axis, wherein the central axis is the axis around which the tire 3 (including the rim on which it is fitted when in use) later rotates on the vehicle. This central axis is not represented and in the embodiment example runs horizontally in the plane of drawing. In order to be able to represent the invention well, the tire 3 is only represented in the region of its tread 10 and its side walls 11, wherein this region is represented in a sectional view.

Within the rubber of the tire 3, both in the region of its tread 10 and in the region of its side walls 11, cords 7 made of metal wires are arranged. For reasons of clarity, only a single cord 7 is represented, in the region of the tread 10 of the tire 3. However, a person skilled in the art is perfectly familiar with how the cord plies within the rubber of the tire 3 run.

The X-ray radiation 4 emitted in the shape of a fan by the X-ray tube 1 in the embodiment example penetrates the tire 3 and is detected in the detector 2, wherein this results in an X-ray radiography image of the tire 3 in the represented sectional plane.

In order to be able to comment on whether the cords 7 in a specific tire type are in the desired positions, the X-ray inspection system must be specifically calibrated to each tire type. Only then is it possible to comment on the quality of the tire 3 with respect to the position and geometry of the cords 7. The need for a calibration in each case to every tire type results from several considerations: tires 3 can have different sizes, different cross-sectional geometries, different thicknesses in the region of the tread 10 and of the side walls 11, the position and the geometry of the cords 7, which in the normal case are grouped together to form bands of cords, can be arranged or formed differently, etc.

According to the invention, the calibration takes place in that the X-ray tube 1 is moved from its starting position represented in FIG. 1 in the movement direction 12 perpendicularly downwards, i.e. also perpendicularly to the tread 10 of the tire 3, into its end position represented in FIG. 2, and at the same time captures of X-ray radiography images of the tire 3 are generated continuously in the X-ray detector 2 and these are then collected in order to then perform data processing on them.

In order to be able to carry out a calibration, in the case of the method according to the invention it is necessary to track the image of a specific cord 7 on the X-ray detector 2 during the whole travel of the X-ray tube 1 in the movement direction 12, with the result that at the end of the movement process both the image 8 of the cord 7 in the starting position of the X-ray tube 1 (see FIG. 1) and its image 9 in the end position of the X-ray tube 1 (see FIG. 2) are known. It is only possible to determine the distance between these two images 8, 9 if the specific cord 7 can be tracked with respect to its image 8, 9 during the whole travel of the X-ray tube 1 and the X-ray image can always be mapped to this.

In FIG. 2, both the X-ray beam 6 in the end position of the X-ray tube 1 (which in this figure passes through the specific cord 7) and the X-ray beam 5 in the starting position of the X-ray tube 1 according to FIG. 1 are represented. It can thereby clearly be seen what distance is present between the two images 8, 9 of the cord 7 in the starting position and the end position. Because of the geometry of the X-ray inspection system as a whole, i.e. of the constituent parts thereof with respect to each other and to the positions of the X-ray tube 1, in particular the starting position and end position thereof, the position of the cord 7 within the rubber of the tire 3 can be deduced both in the vertical and in the horizontal direction according to the representation in FIGS. 1 and 2. The position of the X-ray tube 1 and of the X-ray detector 2 are known because of the design. The distance between them is thus likewise known. The travel path of the object—cord in the tire—is likewise known due to the design, or due to corresponding electromechanical measurement systems. From the pixel size of the X-ray detector 2 and the migration of the cord 7 as an image on the X-ray detector 2, the path of the migration can be converted into a length measurement. There is thus sufficient information available to calculate the distance of the object—cord 7 in the tire—from the X-ray detector 2. With this information and the known pixel size of the X-ray detector 2, elements in the cord plane in the tire 3 can be precisely measured in the X-ray image.

Figure 7:
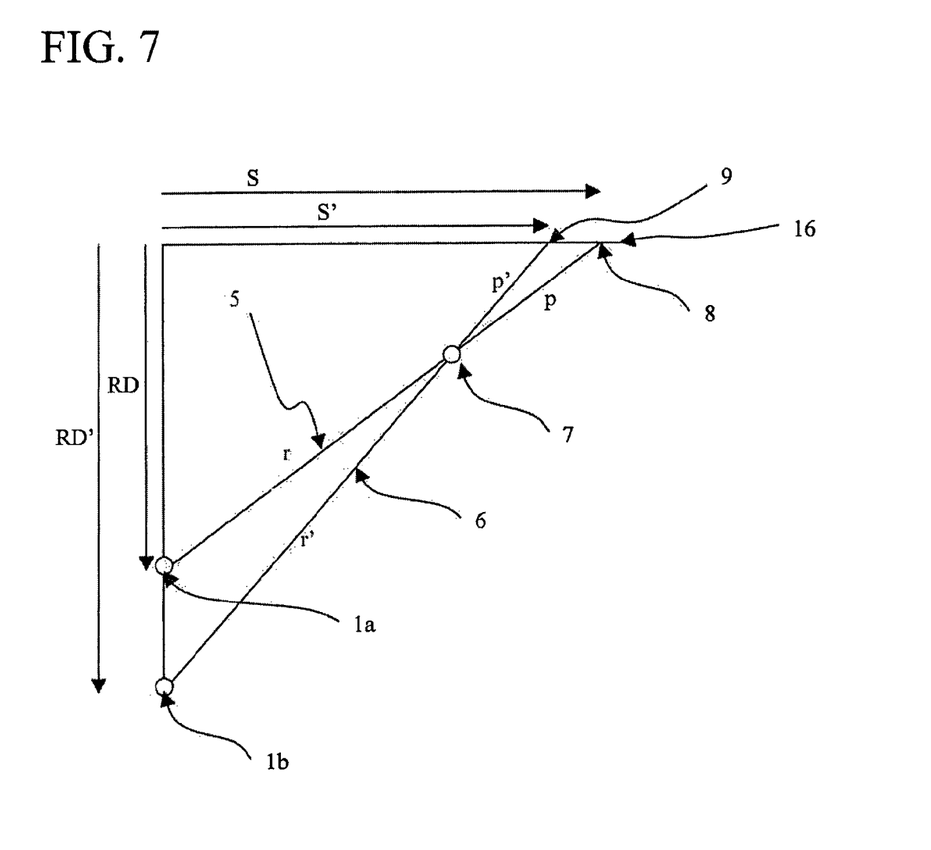
FIG. 7 depicts a diagram illustrating the geometric relationships and the calculation of the magnification, according to an embodiment of the invention.

The conditions described above result—this is clear to a person skilled in the art on the basis of the relationships which are represented in FIG. 7 even without needing to discuss it in more detail here—as the formula for the magnification:

$$\frac{r+p}{r} = \frac{S' * RD - S * RD'}{S' * RD - S' * RD'}$$

With the meanings: r real focus-object distance with X-ray tube 1 in starting position 1a; r' real focus-object distance with X-ray tube 1 in end position 1b; p real object-detector distance with X-ray tube 1 in starting position 1a; p' real object-detector distance with X-ray tube 1 in end position 1b; RD distance of the X-ray tube 1 in starting position 1a from the detector plane 16; RD' distance of the X-ray tube 1 in end position 1b from the detector plane 16; S distance of the image 8 of the cord 7 in starting position from the point of origin; S' distance of the image 9 of the cord 7 in end position from the point of origin.

The (known) X-ray line detector which is used as the X-ray detector 2 has detector elements which routinely have a determined defined size—in this case of approx. 0.5 mm. The resolution of the X-ray line detector depends on this width of the detector elements. In addition, this resolution depends on the pixel width on the screen on which the X-ray radiography image is observed. The image of a detector element can always only be either black or white, depending on whether at its position precisely one cord 7 is in the beam path of the X-ray tube 1 or not. In the case of a greater magnification, two or more detector elements can also represent a single cord 7.

Because of these circumstances, it is possible in the case of a sufficiently high reading rate of the X-ray detector 2 to trace the migration of the image 8, 9 of the specific cord 7, as the place in which the detector element reproduces a black image, which thus corresponds to the specific cord 7, has migrated further in the subsequent X-ray radiography image by at most one detector element or, as the case may be, is also still in the same detector element. In order to enable such a tracking of the specific cord 7, the reading rate is in the region of 0.5 ms with a movement speed of the X-ray tube 1 in movement direction 12 of approx. 1.5 m/min. The travel path of the X-ray tube 1 from its starting position represented in FIG. 1 into its end position represented in FIG. 2 is approx. 100 mm, which results in a travel time of approx. 4 seconds. It is thereby possible, because of the light-dark information of the individual detector elements and their sequence, to track the specific cord 7 in the X-ray radiography images.

As there is more time available in the calibration to a new tire type than later in the inspection of an individual tire 3 (here a throughput that is as high as possible must be maintained), the travel time of 4 seconds is not an overly disruptive problem. Due to the information obtained during the calibration method according to the invention, after that it is possible in the inspection of the individual tires 3 to obtain a very high throughput, as only a single X-ray radiography image of the tire 3 is needed in each angle position to be inspected. Because of the imaging of the specific X-ray radiography image in the inspection, the position and the geometry of the cords 7 can be deduced on the basis of the data obtained in the calibration method according to the invention, and thus it is possible to comment on the quality of the just-inspected tire 3 in an extremely short inspection time.

In the first embodiment example according to FIGS. 1 and 2, in which the X-ray tube 1 is moved in the movement direction 12 during the calibration, the image 8, 9 of a cord 7, which is to the right of the centre of the tread 10 in the drawings, shifts towards the left in the course of the movement of the X-ray tube 1 downwards. The achieved distance between the image 8 of the cord 7 in the starting position of the X-ray tube 1 and the image 9 of the cord 7 in the end position of the X-ray tube 1 is proportional to the path of the X-ray tube 1 multiplied by the value of the set magnification minus 1. For geometrical reasons, no shift takes place for X-ray beams which are perpendicular to the tread 10.

Figure 3:
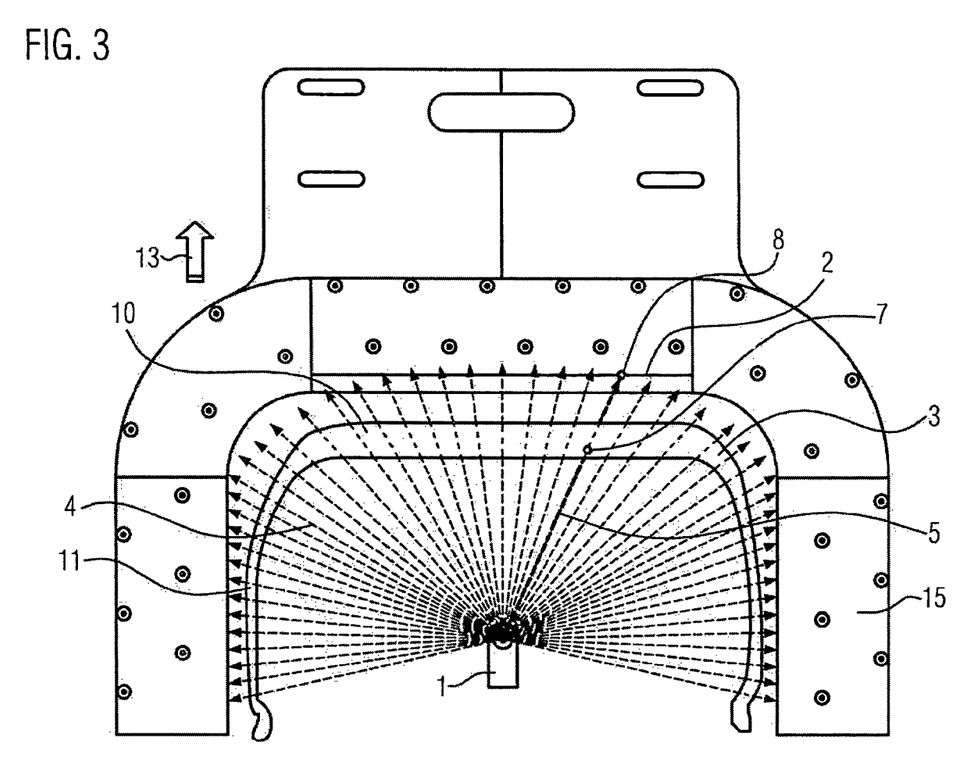
FIG. 3 depicts a representation of another inspection system according to an embodiment of the invention with a movable detector in its starting position.
Figure 4:
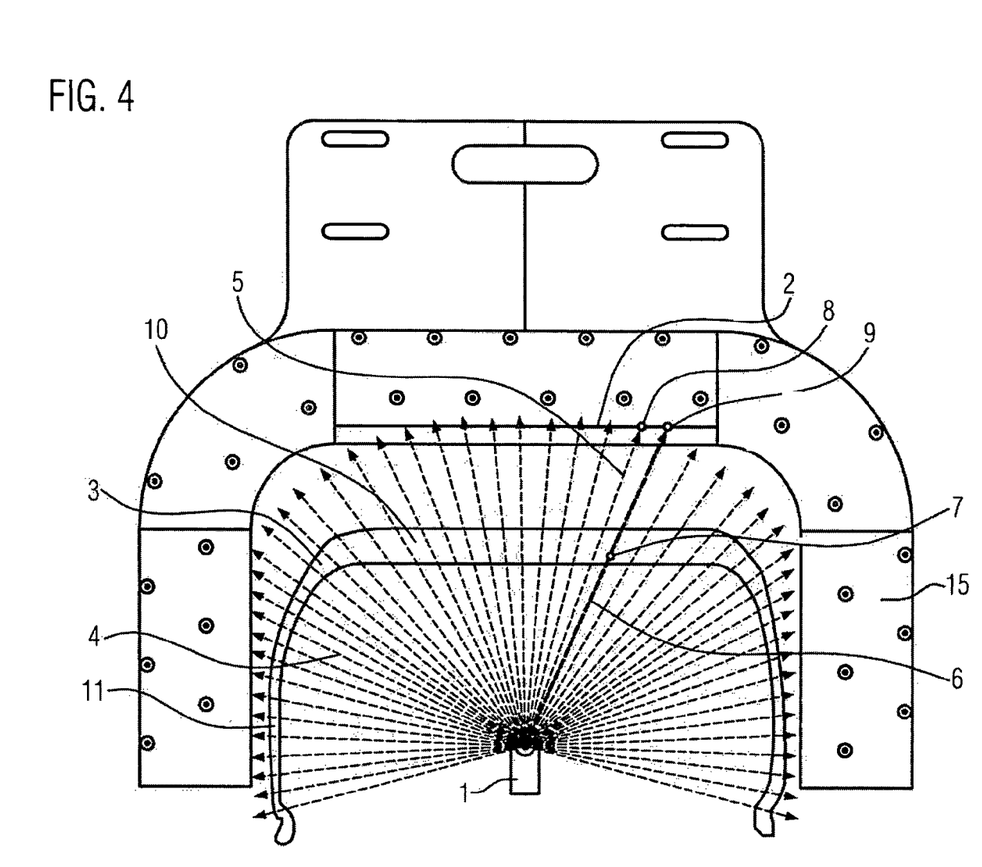
FIG. 4 depicts the X-ray inspection system according to FIG. 3 with the movable detector in its end position.

The calibration takes place in the second embodiment example according to the invention according to FIGS. 3 and 4 in principal in the same way as in the first embodiment example of FIGS. 1 and 2. The difference between the first embodiment example and the second embodiment example is that, unlike in the first embodiment example, the X-ray tube 1 is not moved, but rather the detector 2 is moved in a movement direction 13, which is directed perpendicularly to the tread 10 of the tire 3—vertically upwards in the figures. However, as can be seen in particular from FIG. 4, in which both the X-ray beam 5 in the starting position of the X-ray detector 2 and the X-ray beam 6 in the end position of the X-ray detector 2 are represented, together with the corresponding images 8, 9 of the cord 7, it results here that for a cord 7, which is arranged to the right of the centre of the tread 10, a shift of its image 8, 9 towards the right takes place. In addition, the total shift of the image 8, 9 of the cord 7 between the starting position and the end position of the X-ray detector 2 is larger than in the first embodiment example. The shift is proportional to the value of the set magnification minus 1. Because, as a rule, the magnification lies close to 1, the movement of the X-ray detector causes a larger shift than when the X-ray tube 1 is shifted by the same path.

Figure 5:
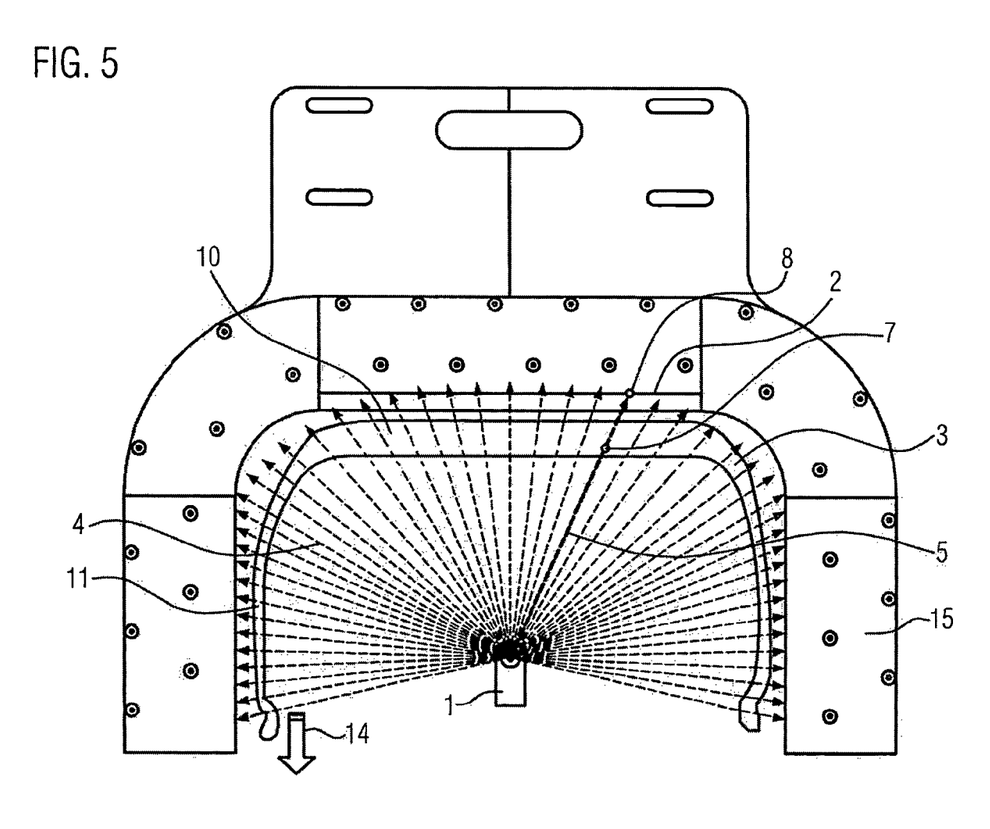
FIG. 5 depicts a representation of a further X-ray inspection system according to an embodiment of the invention with a movable manipulator, wherein the tire fixed to the manipulator is located in its starting position.
Figure 6:
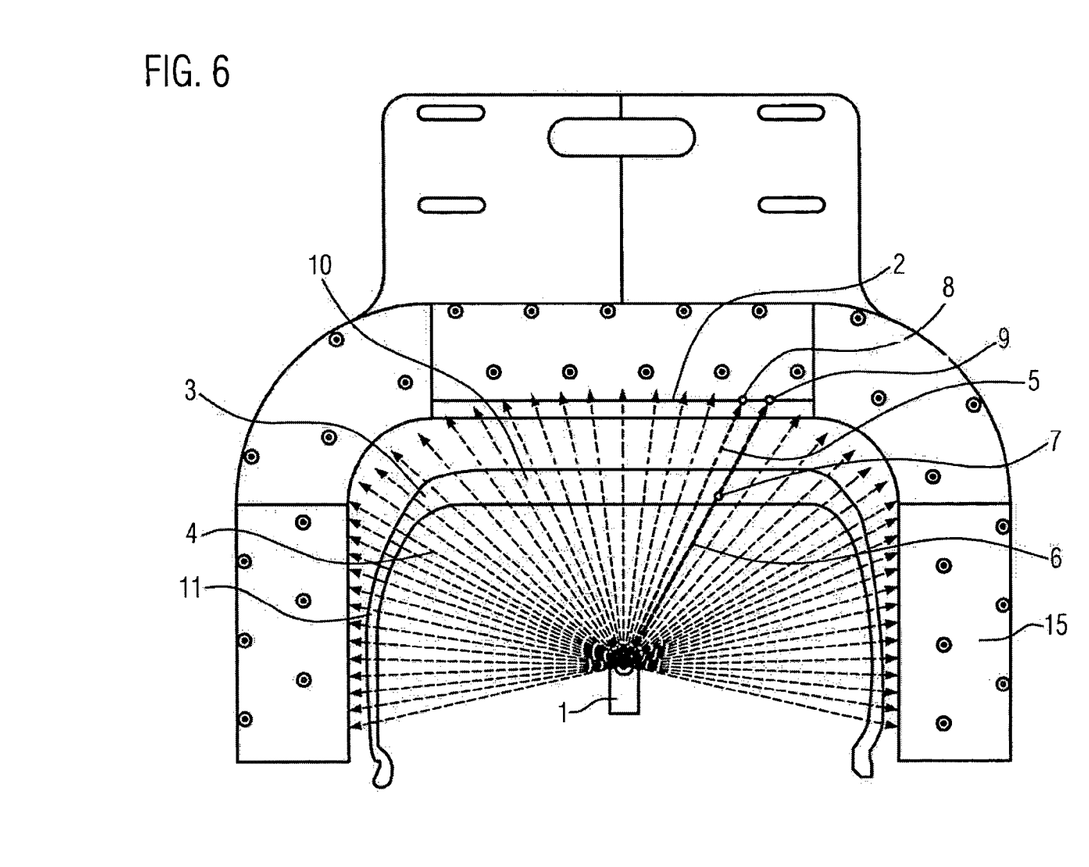
FIG. 6 depicts the X-ray inspection system according to FIG. 5 with the manipulator in its end position.

An even larger shift of the image 8, 9 of the cord 7 is obtained if, in accordance with the third embodiment example of FIGS. 5 and 6, both the X-ray tube 1 and the X-ray detector 2 are left in their places and the manipulator, and thus the tire 3, is moved between the X-ray tube 1 and the X-ray detector 2.

In FIG. 5 the tire 3 is represented in its starting position, very close to the X-ray detector 2. The X-ray beam 5 through the cord 7 generates the image 8 on the X-ray detector 2.

A travel of the manipulator (not shown) and thus of the tire 3 takes place along the movement direction 14, thus perpendicularly to the tread 10 of the tire 3 vertically downwards, until the position of the tire 3 according to FIG. 6 is reached.

In FIG. 6, both the X-ray beam 5 in the starting position and the X-ray beam 6 in the end position through the cord 7 are represented. As in the second embodiment example of FIGS. 3 and 4, when the X-ray detector 2 is shifted a cord 7 which is located to the right of the centre of the tread 10 also migrates towards the right when the manipulator is shifted according to the third embodiment example of FIGS. 5 and 6. However, with the same travel path the shift between the images 8, 9 of the cord 7 between starting position and end position of the manipulator/tire 3 is even larger than in the second embodiment example. The shift here is approximately proportional to the set magnification.

The invention can be briefly summarized as follows with regard to the calibration method: the shift of an image 8, 9 of a cord 7 can only just be determined using two images in the end positions of the shifted unit (X-ray tube 1, X-ray detector 2 or manipulator/tire 3), as there are a large number of cords 7 in the tire 3 and a clear mapping of the cords 7 from the image 8 in the starting position and in the image 9 of the end position is almost impossible. According to the invention, therefore, in a stationary tire (by which is meant that the tire 3 is not rotating—a linear movement as described for the third embodiment example of FIGS. 5 and 6 does not come under this), the movement of one of the three above-named components is carried out and X-ray radiography images are collected during the entire movement. In these X-ray radiography images, which are captured by means of the line detector, a few cords 7 (to improve clarity, in the above-described embodiment examples only one cord 7 is referred to in each case), selected by mouse click in the X-ray radiography image, over the tread 10 and the side walls 11 are used for the tracking in the image sequence. As the reading of the X-ray detector 2 takes place significantly more quickly than the movement of the respective unit, the shift in the images 8, 9 of the cords 7 is very small. Because of the small changes from X-ray radiography image to X-ray radiography image, the cords 7 are not lost in the sequence. Regarding the respectively used cords 7, the position in image 8 in the starting position and in image 9 in the end position is thus determined. The shift (for example orthogonally with respect to the tire surface) is calculated from this. Cords 7 which, in the second embodiment example,—thus in the case of the shift of the detector 2—are closer to the surface of the tread 10—thus the outer side of the tire 3—are shifted less markedly than cords 7 which are closer to the inner side. The position of the cords 7 and the geometry of the tire 3 can thus be calculated from the shifts of the respectively tracked cords 7.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMBERS

1 X-ray tube
1a Starting position of the X-ray tube
1b End position of the X-ray tube
2 X-ray detector
3 Tire
4 X-ray radiation
5 X-ray beam in starting position
6 X-ray beam in end position
7 Cord
8 Image of the cord in starting position
9 Image of the cord in end position
10 Tread
11 Side wall
12 Movement direction of the X-ray source
13 Movement direction of the X-ray detector
14 Movement direction of the manipulator
15 Housing
16 Detector plane

The invention claimed is:

1. A method for calibrating an X-ray inspection system for a tire, which includes an X-ray tube, a linear X-ray detector, and a manipulator for the tire, wherein the manipulator is arranged such that the tire is arranged with its tread between the X-ray tube and the X-ray detector, the method comprising:
    moving one of the X-ray tube, the linear X-ray detector, and the manipulator along a travel path from a set starting position to a set end position;
    capturing, at a preset reading rate during the movement of one of the X-ray tube, the linear X-ray detector, and the manipulator, a continuous capture of X-ray radiography images of a cord within the tire;
    tracking the cord using successive X-ray radiography images; and
    deducing an absolute position of the cord using a total shift of the cord in the X-ray radiography images between the starting position and the end position and using known geometric data.

2. The method according to claim 1, wherein moving one of the X-ray tube, the linear X-ray detector, and the manipulator comprises moving the manipulator.

3. The method according to claim 1, wherein the movement of one of the X-ray tube, the linear X-ray detector, and the manipulator takes place over a travel path of from 50 to 200 mm.

4. The method according to claim 1, wherein the travel path runs perpendicularly to the tread of the tire.

5. The method according to claim 1, wherein the preset reading rate is 0.1 to 10 ms.

6. The method according to claim 1, wherein the speed of the movement of one of the X-ray tube, the linear X-ray detector, and the manipulator is 1 to 2 m/min.

7. A method for inspecting a position of a cord in a tire in an X-ray inspection system after implementing the calibration method according to claim 1, the method comprising:
    capturing only one X-ray radiography image of the tire to be inspected in a particular position of one of the X-ray tube, the linear X-ray detector, and the manipulator, and
    deducing, from a comparison of the only one X-ray radiography image of the tire to be inspected and values obtained from the calibration method, an absolute position of the cord within the tire.

8. The method according to claim 7, wherein the only one X-ray radiography image is captured in a starting position or an end position of one of the X-ray tube, the linear X-ray detector, and the manipulator.

* * * * *